US012702656B2

(12) United States Patent
Zolentroff

(10) Patent No.: US 12,702,656 B2
(45) **Date of Patent: *Aug. 11, 2026**

(54) ALA AND SALT FORMULATION

(71) Applicant: Molecular Product Management LLC, New York, NY (US)

(72) Inventor: William C. Zolentroff, New York, NY (US)

(73) Assignee: Molecular Product Management, LLC, New York, NY (US)

( * ) Notice: Subject to any disclaimer, the term of this patent is extended or adjusted under 35 U.S.C. 154(b) by 1080 days.

This patent is subject to a terminal disclaimer.

(21) Appl. No.: 17/332,955

(22) Filed: May 27, 2021

(65) Prior Publication Data

US 2021/0283102 A1 Sep. 16, 2021

Related U.S. Application Data

(63) Continuation of application No. 16/112,757, filed on Aug. 26, 2018, now abandoned, which is a continuation of application No. PCT/US2017/053845, filed on Sep. 27, 2017.

(60) Provisional application No. 62/506,590, filed on May 15, 2017, provisional application No. 62/400,532, filed on Sep. 27, 2016.

(51) Int. Cl.

| | |
|---|---|
| ***A61K 31/385*** | (2006.01) |
| ***A61K 9/00*** | (2006.01) |
| ***A61K 9/20*** | (2006.01) |
| ***A61P 5/34*** | (2006.01) |
| ***A61P 15/08*** | (2006.01) |
| ***A61P 25/02*** | (2006.01) |

(52) U.S. Cl.

CPC .......... *A61K 31/385* (2013.01); *A61K 9/0056* (2013.01); *A61K 9/2009* (2013.01); *A61K 9/2018* (2013.01); *A61K 9/2095* (2013.01); *A61P 5/34* (2018.01); *A61P 15/08* (2018.01); *A61P 25/02* (2018.01)

(58) Field of Classification Search

None

See application file for complete search history.

(56) References Cited

U.S. PATENT DOCUMENTS

| | | | |
|---|---|---|---|
| 5,527,539 A | 6/1996 | Sarlikiotis | |
| 6,191,162 B1 | 2/2001 | Byrd | |
| 6,271,254 B1 | 8/2001 | Heinz | |
| 6,620,425 B1 | 9/2003 | Gardiner | |
| 7,858,655 B2 | 12/2010 | Roehnert | |
| 9,265,753 B2 | 2/2016 | Benjamin, Jr. | |
| 10,993,929 B2 * | 5/2021 | Heuer | |
| 2004/0265357 A1 | 12/2004 | Karmer | |
| 2007/0190114 A1 | 8/2007 | Smart | |
| 2007/0196442 A1 * | 8/2007 | Heuer | A23L 33/12 514/440 |
| 2008/0095741 A1 | 4/2008 | Wessel | |
| 2009/0004281 A1 | 1/2009 | Nghiem | |
| 2009/0104171 A1 | 4/2009 | Pardee | |
| 2010/0062988 A1 * | 3/2010 | Chen | A61K 9/2063 514/23 |
| 2013/0136703 A1 | 5/2013 | Benjamin | |
| 2016/0235709 A1 | 8/2016 | Benjamin, Jr. | |
| 2020/0246270 A1 | 8/2020 | Bauer | |
| 2021/0069117 A1 | 3/2021 | Vaka | |

FOREIGN PATENT DOCUMENTS

| | | |
|---|---|---|
| CA | 2135535 | 5/1995 |
| CN | 101185701 | 5/2008 |
| DE | 4035442 | 5/1991 |
| DE | 20207569 | 12/2002 |
| DE | 20040010021 | 9/2004 |
| EP | 654484 | 4/2003 |
| JP | 2006219467 | 8/2006 |
| KR | 20070110729 | 11/2007 |
| WO | 2009001362 | 12/2008 |
| WO | 20100127297 | 11/2010 |
| WO | WO2013115736 A2 | 8/2013 |
| WO | WO2018064238 A1 | 4/2018 |

OTHER PUBLICATIONS

Benjamin, et al, ALA Burning Taste Comparison Data (from 15 Respondents on a 1-5 scale).

Benjamin, et al, "The Oral Irritation or Burning due to ALA Concentrations in Buccal Applications", dated Jul. 23, 2015.

Kallai, et al, "Evaluation of Drug Release from Coated Pellets Based on Isomalt, Sugar & Microcrystalline Cellulose Inert Cores", AAPS PharmSciTech, vol. 11, No. 1, Mar. 2010, pp. 383-391.

Mauldin, "The Benefits of Alpha Lipoic Acid", Mar. 24, 2012.

McLlduff, et al, "Critical Appraisal of the use of Alpha Lipoic Acid (Thriocticard) in Treatment of Symptomatic Diabetic Polyneuropathy", Therapeutics and Clinical Risk Management, Sep. 5, 2011, pp. 377*385.

Mijnhout, et al "Alpha Lipoic Acid of Symptomatic Peripheral Neuropathy in Patients with Diabetes: A Meta-Analysis of Randomized Controlled Trials", International Journal of Endocrinology, vol. 2012, Article ID 45679, 8 Pages.

(Continued)

*Primary Examiner* — Clinton A Brooks

*Assistant Examiner* — Nicola Maria Bauer

(74) *Attorney, Agent, or Firm* — Transformative Legal, LLC; Len S. Smith

(57) ABSTRACT

The addition of a salt to an ALA formulation that is dissolved in the mouth unexpectedly significantly reduces the degree of burning or irritation from ALA exposure during administration. This invention is particularly useful for an oral dissolved form of administration due to the extended time of ALA exposure that is possible with such formulations. The salt-inclusive formulations of the invention can increase efficacy of the ALA administration, reduce negative side effects, or both.

25 Claims, No Drawings

(56) References Cited

OTHER PUBLICATIONS

Shay, et al, "Alpha-lipoic Acid as a Dietary Supplement: Molecular Mechanisms and Therapeutic", Biochim Biophys Acta. Oct. 2009, 1790 (10): 1149-1160.
Zieglar, et al, "Treatment of Symptomatic Diabetic Polyneuropathy with Antioxidant Alpha-Lipoic Acid 7-month Multicenter randomized Controlled Trial (Aladin III Study). Aladin III Study Group Alpha-Lipoic Acid in Diabetic Neuropathy", Diabetics Care, 22(8) 1296-301, Sep. 1999.
Non-Final Office Action issued to U.S. Appl. No. 15/050,462 on Oct. 2, 2017.
International Search Report for PCT/US2012/043357 issued Jan. 24, 2013.
International Written Opinion for PCT/US2012/053557 issued Jan. 24, 2013.
Indian Office Action based on PCT/US2012/053357 issued Apr. 9, 2018.
European Search Opinion based on PCT/US2012/053357 issued Dec. 23, 2014.
European Search Report for PCT/US2012/052267 issued Dec. 23, 2014.
International Search Report for PCT/US2017/53845 dated Jan. 30, 2018.
Applicant Amendment Filed with RCE in previously allowed U.S. Appl. No. 16/212,667 (now issued).
European Patent Office Examination Report on Jul. 11, 2023 for 17857376.2.
Non-Final Office Action on May 30, 2019 for U.S. Appl. No. 16/212,667.
International Written Opinion on Jan. 30, 2018 for PCT/US2017/053845.
European Search Report on May 15, 2020 for EP17857376.
Non-Final Office Action on Oct. 4, 2019 for U.S. Appl. No. 16/112,757.
Final Office Action on Apr. 15, 2020 for U.S. Appl. No. 16/112,757.
Applicant Response to Final Office Action on Jun. 20, 2020 for U.S. Appl. No. 16/112,757.
Non-Final Office Action on Feb. 2, 2021 for U.S. Appl. No. 16/112,757.
Bala, et al. "Orally Dissolving Strips: A New Approach to Oral Drug Delivery System." International Journal of Pharmaceutical Investigation, 2013, vol. 3, Issue 2.
Bankar, et al. "A Review on Orodispersible Tablets Prepared Using Spray Dried Sustained Release Microparticles." Journal of Advanced Drug Delivery 2014; 1(2); 82-95.
Bhowmik, et al. "Tablet Manufacturing Prcoess and Defects of Tablets." Elixer Pharmacy, 70 (May 2014) 24368-24374.
Drug Development & Delivery. "Controlled Release Leveraging Precision Particle Fabrication Technology to Create Patient-Friendly Dosage Forms." Web Article; May 2017.
Garbacz et al. "Dissolution of Mesaliazine Modified Release Tablets Under Standard and Bio-Relevant Test Conditions." Journal of Pharmacy and Pharmacology, Feb. 2015, 67(2): 1999-208.
Gupta et al., "Orodispersible Tablets: An Overview of Formulation and Technology." World Journal of Pharmacy and Pharmaceutical Sciences, vol. 9, Issue 10, 1406-1418. Oct. 2020.
Hannan et al. "Oral Dispersible System: A New Approach in Drug Delivery System." Indian Journal of Pharmaeutical Sciences, Jan.-Feb. 2016; 78(1): 2-7.
Krajacic et al. "Matrix Formulation in Sustained Release Tablets: Possible Mechanism of Dose Dumping." International Journal of Pharmacuetics, Jan. 30, 2003; 251 (2-2): 67-78.
Laffleur et al. "Advances in Drug Delivery Systems: Work in progress still needed?" Elsevier (2019). Https://doi.org/10.1016/j.ijpx.2020.100050. Available online Sep. 22, 2020.
Maderuelo et al. "Critical Factors in the Release of Drugs from the Sustained Release Hydrophilic Matrices." Journal of Controlled Release, vol. 154, Issue 1, Aug. 25, 2011, pp. 2-19. Epub Apr. 8, 2011.
Non-Final Office Action on Oct. 4, 2019 for U.S. Appl. No. 16/261,444.
Final Office Action on Apr. 6, 2020 for U.S. Appl. No. 16/261,444.
Non-Final Office Action on May 20, 2020 for U.S. Appl. No. 16/102,711.
Non-Final Office Action on Oct. 23, 2020 for U.S. Appl. No. 16/261,444.
Final Office Action on Dec. 22, 2020 for U.S. Appl. No. 16/102,711.
Final Office Action on Mar. 9, 2021 for U.S. Appl. No. 16/261,444.
Non-Final Office Action on Oct. 20, 2021 for U.S. Appl. No. 16/261,444.
Final Office Action on May 12, 2022 for U.S. Appl. No. 16/261,444.
Prajapati et al. "Formulation Design Approach to Avoid Dose Domping." Pharmaceutics and Pharmaceutical Technology, S.K. Patel College of Pharmaceutical Education & Research. 12 pages. Feb. 2008.
Sharma, Dr. Shaweta. "Recent Research in Pharmaceutical Sciences." Galgotias University, Weser Books, No. 79737. vol. 1, 2021. Aug. 2021.
Thomas, Felicity. "Taking a Controlled Approach." Pharmaceutical Technology, Jul. 1, 2020. vol. 44, Issue 7, pp. 26-29.
Uddin. "Advanced Drug Delivery Systems." Available via slideshare at slideshare.net/JalalUddin.10/advanced-drug-delivery-system. Uploaded Jan. 11, 2018.

* cited by examiner

ALA AND SALT FORMULATION

CROSS-REFERENCES TO RELATED APPLICATIONS

This Application is a continuation of, and claims priority to, co-pending U.S. patent application Ser. No. 16/112,757, filed Aug. 26, 2018, entitled "ALA AND SALT FORMULATION," which claims the benefit of priority to PCT application PCT/US17/53845 (publication number WO/2018-064238) filed Sep. 27, 2017, which claims the benefit of priority to U.S. Provisional Patent Application 62/506,590, filed May 15, 2017 (referred to herein as "Salt Provisional-II"), and U.S. Provisional Patent Application 62/400,532, filed Sep. 27, 2016 (referred to herein as "Salt Provisional-I"). This application claims priority to, and incorporates the entirety of, each one of the above-referenced priority Applications.

FIELD OF THE INVENTION

This application is directed to oral dissolve pharmaceutical compositions of alpha-lipoic acid and one or more salts and their related delivery and treatment methods.

INCORPORATION BY REFERENCE

The patent titled: LIMITED RELEASE LINGUAL THIOCTIC ACID DELIVERY SYSTEMS, application Ser. No. 13/602,093, U.S. Pat. No. 9,265,753, issued Feb. 23, 2016 with the primary inventor Benjamin is hereby incorporated by reference (and hereinafter may be referred to as "Benjamin Patent"). Additionally, the patent application (a Continuation-in-Part) titled: LIMITED RELEASE LINGUAL THIOCTIC ACID DELIVERY SYSTEMS, application Ser. No. 15/050,462, with a filing date: Feb. 22, 2016 and the primary inventor Benjamin is hereby incorporated by reference (and hereinafter referred to as "CIP Application" or by application Ser. No. 15/050,462). The incorporated references are intended to broaden the scope of this disclosure and to provide context and information that may be missing from this disclosure. These incorporations are not intended to hamper this disclosure, specifically, the term "tablet" or "compressed tablet" may be substituted, when appropriate, for the term "lozenge" to update the incorporated text. For any information that conflicts between these incorporations and this disclosure, the content of this disclosure shall prevail over such conflicting information in the incorporated references.

BACKGROUND OF THE INVENTION

Alpha-lipoic acid or ALA has two chiral enantiomers. It is found as R-(+)-lipoic acid (RLA) and S-(−)-lipoic acid (SLA). Quite commonly, ALA is found as a racemic mixture of the two R/S-Lipoic acids. Additionally, each of these thioctic acid enantiomers exist in reduced (dihydro-lipoic acid) and oxidized forms. The disclosures herein are generally effective for any and/or all of the above ALA variants. The term thioctic acid, alpha-lipoic acid, or ALA refers to all of these various species of lipoic acid, unless specifically referred to otherwise.

ALA is commonly used as a health supplement and also is helpful in treating a variety of diseases, particularly those involving blood sugar problems such as type II diabetes and diabetic neuropathy. The intravenous (I.V.) delivery of ALA has proven to be more effective than the ingested supplement, particularly for diabetic neuropathy. However, on an ongoing basis, particularly weekly or daily, administration is impractical.

Prior application Ser. No. 13/602,093 (now issued U.S. Pat. No. 9,265,753) and its related continuation-in-part (CIP), application Ser. No. 15/050,462, have disclosed that a lozenge or tablet that dissolves in the mouth releasing ALA can provide ALA to the bloodstream in quantities more similar to IV than traditional supplements. The problem is that releasing too much ALA at any given time causes oral irritation and burning. To solve this, the Ser. Nos. 13/602,093 and 15/050,462 applications provide for a slow, steady dissolution of the formulation and appropriate, fairly low, concentrations of ALA. The limitation of this solution is that it can take longer than desired to get to a higher dose of ALA, for example 600 mg.

BRIEF SUMMARY OF THE INVENTION

The addition of a salt to an ALA formulation reduces the degree of burning or irritation from ALA exposure during administration. This is particularly useful for an oral dissolve form of administration due to the extended time of ALA exposure. This salt-inclusive formulation either increases the efficacy of the ALA administration, reduces negative side effects, or both. This occurs because the formulation can have higher concentrations of ALA or faster dissolution times than a formulation that does not include salt. In turn, this allows larger amounts of ALA to be released more rapidly, which means larger amounts of ALA enter the bloodstream more rapidly without causing undue irritation. This can also reduce the time required to administer an efficacious dose and/or reduce the size of each dose or number of doses associated with the formulation.

DETAILED DESCRIPTION OF THE INVENTION

This disclosure describes means by which tablets, lozenges, troches, gummies, gum and/or the like containing noticeable, reasonable, significant, and/or effective amounts of ALA (alpha lipoic acid, also known as thioctic acid) may be made or manufactured for administration by dissolving in the mouth. Such means include formulations for administration and related production methods, which result in a tablet or lozenge with an acceptably low (or reduced relative to some other or more typical formulations) burning sensation, and/or irritation, of the oral tissues when such formulation is administered by dissolving the formulation primarily, or entirely, in the mouth. Such administration, referred to as "oral dissolve" administration, includes sublingual, lingual and/or buccal administration and/or oral mucosal absorption; the latter term being more descriptive of the purpose of the ALA formulation and less localized to any particular portion of the mouth. Oral dissolve administration should be interpreted as being distinct from oral administration; oral administration being that the tablet, lozenge, capsule, liquid or the like is swallowed, and its dissolution and absorption does not occur in the mouth, but primarily occurs in the gastrointestinal (G.I.) tract, particularly the intestines.

Note, the burning and/or irritation of tissue from exposure to ALA is referred to in this document as ALA burn effect, ALA burn, ALA burning and/or ALA irritation (or just burn, burning, or irritation when the context implies that it refers to, or is due to, ALA).

Because the ALA burn is not only a problem for the oral tissues but also for the tissues of the G.I. tract, some of the disclosures of this patent application include solutions that reduce the ALA burn caused by ingested ALA delivery, including in the form of tablet, lozenge, capsule, gel, gel cap, liquid and reconstituted liquid forms.

In addition to oral administration, medicinal substances, including the ALA of the present invention, may be delivered by other routes of administration including but not limited to intravenous (I.V.), rectal, dermal, topical, intrathecal, intramuscular or subcutaneous.

The Problem

An advantage of making tablets (by direct compression) that contain ALA for oral dissolve administration is that such tablets are not heated to the high temperatures of a hard candy lozenge (also referred to as hard-crack candy). This eliminates or considerably reduces the degree of ALA polymerization, reduces ALA loss through sublimation, allows the addition of heat sensitive active ingredients such as but not limited to vitamin B1, and allows the addition of ingredients that are best and/or only available in powder form. This may provide the oral dissolve administration of additional active ingredients that are more potently delivered by oral dissolution (again, e.g. vitamin B1). Note, the use of the term "polymerize" as used in the passage above, or when relevant or appropriate, may include and extend beyond its purely scientific meaning of being the result of covalent bonding to include any ALA conglomeration further including solution conglomeration such as the formation of multiple ALA homo and hetero dimers, trimers, and other stable electrostatic and/or hydrophobic/hydrophilic structures (with or without other chemical moieties) that fail to disassociate in an aqueous environment, thereby inhibiting the process of individual ALA molecular dispersion.

Compressed tablets generally have a lower density than hard candy lozenges. Accordingly, to make a compressed tablet with the same concentration and dose of ALA generally requires making the tablet larger than the equivalent hard candy lozenge. It was found that such tablets may be more than twice as large. However, a smaller tablet may achieve the same dose if the concentration of ALA is increased. A higher concentration of ALA is possible with the tablet because the ALA is not polymerized. It appears that the polymerized ALA in the hard candy lozenge creates a sticky film that sticks to the oral tissues and burns the tissue to a greater degree than unpolymerized ALA. From data obtained during comparisons between hard candy lozenge and compression tablet forms, it is hypothesized that ALA polymerization slows, inhibits or prevents the absorption of ALA through the oral tissues and into the bloodstream.

Solutions

It is noted that herein the percentage of ALA, other active ingredients or excipients in the formulation are measured by weight, unless otherwise specified.

It was found that the concentration of ALA in a compressed tablet may exceed that of a hard candy lozenge and still provide an equivalent degree of ALA burn reduction. Such tablet ALA concentration increase ("ALA-CI"), relative to the ALA concentration in a hard candy lozenge, may range between about 10% and 40%, preferably between about 25% and 75%, more preferably between about 50% and 100%, and most preferably between about 90% and 200% (where 0% means the tablet and hard candy ALA concentrations are identical and percent is by weight). For example, a compressed tablet with 12% ALA concentration and hard candy lozenge with 5% ALA concentration would mean the tablet has an additional 7% ALA concentration, making it a 140% higher ALA concentration (140% ALA-CI) than the lozenge and therefore falls within the last range. While a 7.5% ALA tablet having 50% more ALA (50% ALA-CI) than the 5% ALA lozenge, falls within the two middle ranges. Note, the above ranges overlap and therefore may be combined into wider ranges such as a range between 25% and 100% or a range between 10% and 200%.

Another way to talk or think about the 140% ALA-CI example above would be that the 140% increase could be thought of as a multiplying factor of 240%. That is adding 100% to the above numbers and multiplying the hard candy lozenge concentration by that multiplying factor. For example, the hard candy lozenge with a 5% ALA concentration times 240%=12% ALA concentration.

Note, unless the meaning is clearly to the contrary, all ranges set forth herein are deemed to be inclusive of the endpoints. For example, a range between 10% and 40% includes 10% and 40%.

Also note, the term "preferable" is used in the earlier paragraph (and throughout the document) to mean "desirable" rather than "probable" or "best choice". In the above ALA-CI disclosure the lower ranges may be more probable choices (10% and 40%, and 25% and 75%), but the higher ranges are more desirable (50% and 100%, and 90% and 200%). It should be noted, when comparing the order from least to most preferable, that our use is generally in reverse order compared to the traditional use.

However, it may be experientially, experimentally or otherwise determined that alternative, and/or additional, concentrations ranges of tablet ALA to hard candy ALA (ALA-CI ranges) may be more applicable, effective, preferable, and/or Acceptable (Note the term "Acceptable" is defined later in this document under the heading "5 Levels of Acceptability" (and in the Ser. No. 15/050,462 application). The five levels range progressively from Agreeable to Tolerable as follows: Agreeable, Satisfactory, Adequate, Marginal, and Tolerable). Otherwise defined (and/or applied) in a similar fashion to the tablet ALA concentration increase (ALA-CI) ranges previously disclosed in this section, these and/or additional ALA-CI ranges may be specified by selecting one number from a group of low range numbers and selecting one number from a group of high range numbers: the low range number group comprising about 10%, 15%, 20%, 25%, 35%, 40%, 45%, and 50%, 55%, 60%, 65%, 70%, 75%, 80%, 90%, and 95%; and the high range number group comprising about 25%, 35%, 40%, 45%, 50%, 55%, 60%, 65%, 70%, 75%, 80%, 90%, 100%, 125%, 150%, 175%, 200%, 250%, 300%, 350%, and 400% of ALA-CI. For example, selecting 20% from the low range group and 50% from the high range group would be equivalent to specifying an ALA concentration increase (ALA-CI) range between 20% and 50%; or selecting 40% from the low range group and 90% from the high range group means specifying a range between 40% and 90% of ALA-CI, Note, unless stated to the contrary, the numbers from the low range and high range groups which overlap (are replicated in the other group) shall not be selected such that the number from the low range group is higher than the number from the high range group or that both numbers are the identical. This applies, not only to the instance above, but to all low and high range pairings set forth herein.

As noted in the two patents incorporated by reference (application Ser. No. 13/602,093 now U.S. Pat. No. 9,265,753 and application Ser. No. 15/050,462), both the concentration levels of ALA and the rate of ALA release limit and determine the degree of oral tissue ALA burn. To reiterate, the concentration levels of ALA for oral dissolve delivery (given the same release rates) may be increased in a compressed tablet formulation relative to a hard candy lozenge formulation. The simplest way to disclose (or talk/think about) changing the amount of ALA released into the saliva (ALA release rate) is to put it in terms of changing the concentration levels of ALA in the formulation (product, tablet, lozenge etc.) while maintaining similar oral dissolution rates of the compared formulations.

Note however, the ALA release rate may be increased by only increasing the formulation's dissolution rate, or by increasing both the concentration and dissolution rates, such that they are the equivalent of only increasing the concentration level of ALA in the formulation. Therefore the same increased percentages disclosed for ALA-CI lozenge or tablet ALA concentrations may be applied to the equivalent increase in dissolution rates rate of ALA release, or applied to the equivalent increase in ALA release rates. Particularly, the latter, because whether the ALA concentration is increased or the dissolution rate is increased, ultimately they both effect and control the ALA release rate.

In preliminary experiments performed on the hard candy lozenge it was determined that a 3% concentration of ALA was acceptable to most people for oral dissolve use, 6% was marginally acceptable and 9% was unacceptable to most users.

In contrast to hard lozenge data, the ALA concentrations in the compression tablet are generally satisfactory at a 5%, adequate at a 7.5%, and marginally acceptable at 10%. These tablets are circular, 9 mm in diameter, approximately 5 mm thick, having a weight of approximately 0.35 g and dissolution times of about 3.5 minutes.

It was also determined that tablets with 15%, 20%, and even 25% concentrations of ALA cause a high-level burning sensation in the mouth, but in many ways are more acceptable than significantly lower concentrations of the hard candy lozenge, because the hot, burning sensation dissipates rapidly as soon as the ALA tablet is gone (fully dissolved).

Some of the ALA in the saliva is swallowed during oral dissolve administration, therefore the esophagus and stomach encounter some ALA and may be irritated by it, particularly in humans and non-human species with sensitive stomachs. Some individuals have found that an antacid such as calcium carbonate (e.g., Turns, etc.) reduces this stomach irritation when taking ALA orally (reminder: "orally" means taken through the mouth and primarily ingested and absorbed in the G.I. tract, but not primarily orally dissolved). Not to be bound by theory, the working hypothesis is that most of the ALA burn is due to the biological activity of the ALA (apoptotic effect) rather than the acidic quality of the ALA which is rather mild (pKa=4.7). Reducing the acidity may be helpful, but has a minimal effect, if any, on the ALA burn.

Trying sodium bicarbonate ($NaHCO_3$) as an alternative to calcium carbonate, revealed that (despite being only mildly alkaline) it has a more pronounced reduction of the ALA burn (burning sensation in the mouth).

Preliminary findings indicate that a 10% ALA tablet with 5% sodium bicarbonate is about as acceptable as a 5% or a 7.5% ALA tablet without the sodium bicarbonate.

However, there is another side effect of oral dissolve ALA delivery which is more subtle than the ALA burn. This varies considerably among different people who have tried the oral dissolve ALA, with some stating their oral tissue feels "raw", "irritated", "aggravated" or "roughened", Some do not experience this effect. Not to be bound by theory, the current working hypothesis is that this is another effect of the ALA flooding into the oral tissue cells and an overabundance of ALA to the mitochondria (the apoptotic burning referred to in the incorporated disclosures).

Despite the large degree to which sodium bicarbonate reduces the burning sensation in the mouth it does not reduce this second issue of tissue rawness. It is conjectured that this surprising result may be due to the fact that sodium bicarbonate is such an integral part of cellular chemistry that the sodium bicarbonate may be increasing the rate at which ALA enters the oral tissue cells.

Note, in this instance a distinction is being made between the term this tissue aggravation/irritation and ALA burn. Otherwise, ALA burn is meant to include this tissue aggravation as a subset of side effects experienced by some users.

Na—R-ALA and Other Alt-ALAs

Note, some manufacturers of R-ALA also manufacture a Na (sodium)-R-ALA; that is, a salt version of the R-ALA in which one of the hydrogen atoms in the ALA molecule is replaced with a sodium atom. They claim that such modified, or alternate form of, ALA creates a much more stable version of R-ALA and that the R-ALA does not polymerize. A manufacturer also makes a potassium version of ALA.

It is observed that it is possible to achieve a further reduction of the ALA burning and/or rawness problems of oral dissolve ALA administration by using Na—R-ALA in place of racemic ALA or R-ALA. Therefore, the effectiveness, as defined as a higher peak concentration of plasma ALA and/or total amount of ALA delivered to the bloodstream while limiting the amount of ALA burn in this instance, of the oral dissolve ALA tablet may be applied to Na—R-ALA (sodium-R-ALA). Furthermore, the oral dissolve ALA tablet's effectiveness could incorporate a sodium version of racemic ALA (or even S-ALA). Lastly, this effectiveness could also apply to other salts besides sodium (for example but not limited to potassium) used to modify either R-ALA, S-ALA or a racemic ALA. These modified versions of ALA will be referred to collectively as "Alt-ALA" to distinguish them from traditional ALA referred to as "Std-ALA" ("Alt" alludes to "alternate"; "Std" alludes to "standard"). To reiterate/clarify, in the Std-ALA form of ALA, the hydrogen atom is not replaced by a salt atom or molecule. For Alt-ALA, the hydrogen atom is replaced by a salt atom or molecule such as sodium, potassium, etc. Put another way, Std-ALA is simply standard ALA while Alt-ALA is a salt version of ALA where sodium or some other cation forms a salt with ALA. That is ALA is acting as the anion in the salt complex.

To clarify a portion of the above paragraph, this is a disclosure of the idea of creating racemic versions of Na—R-ALA and Na-ALA. Furthermore, we propose also creating non-sodium alternative-salt versions of racemic ALA, including K-ALA for example or other cations incorporated into ALA (such as: Na+, K+, Ca2+, Mg2+, Fe2+, Fe3+, Cu+, Cu2+, Mn2+, Mn4+, Co2+, Cr3+, Cr6+, Cd2+, Zn2+). Furthermore, this is a disclosure of using those versions as a means of reducing ALA burn during the administration of ALA, in particular the oral dissolve administration of ALA.

Relative to Std-ALA (racemic ALA, R-ALA and/or S-ALA), different, typically higher, formulation concentrations of Alt-ALA may be used without additional or excessive ALA burn. Such Alt-ALA concentrations in the formulation could range between about 10% and 30%, preferably between about 25% and 100%, more preferably between about 90% and 200%, and most preferably between about 190% and 500% higher than Std-ALA concentrations. Note, the above ranges overlap and therefore may be combined into larger ranges such as a range between 10% and 100% or a range between 25% and 500%. Note, these percentages refer to the percentage of the increase rather than the total ALA concentration in an Alt-ALA formulation. An example of how the percentages work is: if an Alt-ALA can have 20% higher percentage of ALA than a Std-ALA which has a 10% concentration of ALA, then the Alt-ALA would have a 12% concentration of ALA (10%+2%), while 100% higher would result in an Alt-ALA with an ALA concentration of 20%.

However, it may be experientially, experimentally, or otherwise determined that alternative, and/or additional ranges of Alt-ALA concentration relative to Std-ALA concentration may be more applicable, effective, preferable, and/or Acceptable. Otherwise defined (and/or applied) in a similar fashion to the Alt-ALA ranges previously disclosed in this section, these alternative, and/or additional, Alt-ALA ranges may be specified by selecting one number from a group of low range numbers and selecting one number from a group of high range numbers: the low range number group comprising about 1%, 2%, 3%, 5%, 7%, 10%, 12%, 15%, 17%, 20%, 25%, 30%, 40%, 50%, 60%, 70%, and 75%; and the high range number group comprising of about 10%, 15%, 20%, 25%, 30%, 40%, 50%, 60%, 70%, 75%, 80%, 90%, 100%, 125%, 150%, 175%, 200%, 250%, 300%, 400%, 500%, 600%, 700%, 800%, 900%, and 1000%. For example, selecting 25% from the low range group and 150% from the high range group would be equivalent to specifying an Alt-ALA range concentration between 25% and 150% higher than Std-ALA concentrations, or selecting 50% from the low range group and 300% from the high range group would be equivalent to specifying an Alt-ALA range between 50% and 300% higher than Std-ALA concentrations.

Note, there is also the issue of expense. R-ALA is more expensive than racemic ALA and Na—R-ALA and it is considerably more expensive than R-ALA.

Furthermore, there is a debate about the preferred use of racemic ALA and R-ALA. R-ALA is the biologically active isomer and therefore considered preferable by some. However, the racemic ALA (or S-ALA) (which provides a 50-50 mixture of S-ALA and R-ALA) may be superior for non-chiral (achiral) biological reactions such as ALA's antioxidant properties and cellular signaling transduction effects. A reason for this may be that the S-ALA is not biologically consumed by chiral biological reactions (notably mitochondrial metabolic boost) and therefore remains in the bloodstream longer (or possibly cytoplasm) providing extended non-chiral biochemical properties and benefits.

Accordingly, versions of racemic ALA and/or R-ALA that minimize ALA burn may be desirable. The best balance between effectiveness in achieving the desired results from the oral dissolve application of ALA, cost, and the minimization of ALA burn to desired levels may result in formulations (including tablets, lozenges, troches, gummies, other oral dissolve products, or gum, liquids and reconstituted or pre-dissolved liquids) that utilize one of racemic ALA, R-ALA, S-ALA, Na—R-ALA, or other Alt-ALA (collectively "ALA-Group") in a combination with another member(s) of this ALA-Group. For example, the combination of a Std-ALA and an Alt ALA, such as racemic ALA combined with an Na—R-ALA.

The percentage of any one of the above ALA-Group ALAs in relationship to the total ALA in the formulation could range between about 1% and 6%, preferably between about 5% and 20%, more preferably between about 15% and 40%, and most preferably between about 25% and 75%. Note, the above ranges overlap and therefore may be combined into larger ranges such as of one of the ALA-Group ALAs, ranging between 5% and 40% or ranging between 1% and 75%, of total ALA.

However, it may be experientially, experimentally or otherwise determined that alternative, and/or additional, ranges of the ALA-Group ALA concentration may be more applicable, effective, preferable, and/or Acceptable. Otherwise defined (and/or applied) in a similar fashion to the ALA-Group ALA ranges previously disclosed in this section, these alternative, and/or additional, ALA-Group ALA ranges may be specified by selecting one number from a group of low range numbers and selecting one number from a group of high range numbers: the low range number group comprising about 1%, 2%, 3%, 5%, 7%, 10%, 12%, 15%, 17%, 20%, 25%, and 30%; and the high range number group comprising of about 10%, 13%, 15%, 18%, 20%, 25%, 30%, 35%, 40%, 45%, 50%, 55%, 60%, 65%, 70%, 75%, 80%, and 90%. For example, selecting 10% from the low range group and 50% from the high range group would be equivalent to specifying an ALA-Group ALA range between 10% and 50% or selecting 3% from the low range group and 65% from the high range group would be equivalent to specifying a range between 3% and 65% of an ALA-Group ALA.

Because they are used somewhat interchangeably one might expect potassium bicarbonate to work as well as sodium bicarbonate in this application. However, it was determined that it does not reduce the ALA burn nearly as well as sodium bicarbonate. While considerably less effective than sodium bicarbonate it could still have some usefulness for those who must limit their intake of sodium.

5 Levels of Acceptability

The amount of ALA burn that is acceptable to the user can vary between users, but also depends on circumstances. The more important and worthwhile taking the ALA tablet is (for example the higher the level of discomfort or disease state the user is attempting to overcome via use of ALA) the more acceptable a greater amount of ALA burn (or other side effect) may be. Therefore, there is no single level of tolerance or acceptability.

To provide greater specificity on this issue, we have identified, and disclosed, five levels of acceptability ranging from Agreeable to Tolerable. The levels proceed from lower amounts of side effect (that are considered acceptable) to higher. Each level is divided into two subcategories, a and b, respectively representing daily (or everyday) use and intermittent (or occasional) use. Level b would generally be expected to have a higher threshold of acceptable negative side effects than level a, because the user would experience the side effects less often due to the intermittent (or occasional) use. The categories are detailed as follows.

Level-1a is Agreeable for daily use and Agreeable for intermittent use is referred to as Level-1b. That is to say, Level-1a represents an Agreeable response by the average user to a very low threshold of acceptable negative side effects, or no side effects, in daily use. Level-1b represents a slightly higher threshold of acceptable negative side effects. At Level-1 the formulation's side effects are generally not an impediment to use, or even an issue, for most users.

Level-2a is Satisfactory for daily use and Satisfactory for intermittent use is referred to as Level-2b. That is to say, Level-2a represents a Satisfactory response by the average user to a low threshold of acceptable negative side effects in daily use. Level-2b represents a somewhat higher threshold of acceptable negative side effects. At Level-2 the formulation's side effects are noticeable, but generally not an impediment to use for most users.

Level-3a is Adequate for daily use to reduce pain and Adequate for intermittent use is referred to as Level-3b. That is to say, Level-3a represents an Adequate response by the average user to a medium threshold of acceptable negative side effects in daily use. Level-3b represents a somewhat higher threshold of acceptable negative side effects. At Level-3 the formulation's side effects are an impediment to use for many users, but the benefits definitely outweigh the deficits.

Level-4a is Marginal (or Borderline or Preferable to intravenous (I.V.)) for daily use and Marginal for intermittent use is referred to as Level-4b. That is to say, Level-4a represents a Marginal response by the average user to a high threshold of acceptable negative side effects in daily use. Level-4b represents a higher threshold of acceptable negative side effects. At Level-4 the formulation's side effects are an impediment to use for a majority of users, yet the benefits outweigh the deficits, but only marginally. Or that is to say, benefits outweigh the deficits but only when the benefits are fairly considerable. The benefits could include improving serious, and/or severe, medical conditions, and/or reduce severe pain.

Level-5a is Tolerable for daily use to improve extremely severe pain, very severe and/or life-threatening medical conditions. Tolerable for intermittent use is referred to as Level-5b. That is to say, Level-5a represents a Tolerable response, on average, to a very high threshold of acceptable negative side effects in daily use. Level-5b represents the highest threshold of acceptable negative side effects of all Levels, because the use is intermittent or occasional. At Level-5 the formulation's side effects are a significant impediment to use for most users, such that only very significant benefits outweigh the deficits.

To reiterate, the maximum level of ALA concentration and consequent side effects that is acceptable at Level-5b is generally not acceptable at Level-5a or the lower Levels 4 through 1. The maximum level of ALA concentration and consequent side effects that is acceptable at Level-4 is generally not acceptable at Levels-3 or below, and so on.

If values, such as ALA concentration or ALA release rates, are preassigned to the different Levels, the exact order of these levels, particularly Level-4 "Marginal (or Preferable to I.V.)", may be different or altered based on feedback from subject use and tests.

Minor note: the maximum daily concentration and consequent negative side effect threshold would likely be unique for each Level, but we would expect overlap below the maximum levels. For example, if a lozenge with a concentration of 1-3% ALA (and its resulting oral irritation) is acceptable for Level-1a and a lozenge with a concentration of 1-15% ALA is acceptable for Level-5b, then there is an overlap between the two Levels in the 1-3% range.

Also, particular applications might span multiple Levels. For example, Levels 2, 3 and 4 could apply to diabetic neuropathy. And Levels 3, 4 and 5 could apply to later stages of diabetic neuropathy when severe health issues such as open sores or amputation arise. The resulting lexicon for referencing levels of acceptability may be utilized as follows: Agreeable-1, Satisfactory-2, Adequate-3, Marginal-4, Tolerable-5. To specify sub level, denotation as follows: Agreeable-1a (or 1b), Satisfactory-2a (or -2b), Adequate-3a (or -3b), Marginal-4a (or -4b), Tolerable-5a (or -5b). Also, either Level or the adjective name may be used interchangeably, e.g., Level-1 is the same as Agreeable-1.

When the term is capitalized the unique one-word terms may also be used to describe each Level of Acceptability as Agreeable, Satisfactory, Adequate, Marginal, and Tolerable, unless context clearly indicates otherwise. Or when referring specifically to each Level by name it may be followed by a hyphen, the level number and, when distinguishing between daily and intermittent use, the sub level letter a or b, as follows: Agreeable-1, Satisfactory-2, Adequate-3, Marginal-4, Tolerable-5. To specify sub level, denotation as follows: Agreeable-1a (or -1b), Satisfactory-1a (or -2b), Adequate-3a (or -3b), Marginal-4a (or -4b), Tolerable-5a (or -5b). Also, either Level or the adjective name may be used interchangeably, e.g., Level-1 is the same as Agreeable-1.

Additionally, when the term is capitalized, the term Acceptable refers to the entire range of these five levels (Agreeable, Satisfactory, Adequate, Marginal, and Tolerable) of acceptability, unless context clearly indicates otherwise.

The 5 Levels of Acceptability may be referred to herein as: Agreeable-1, Satisfactory-2, Adequate-3, Marginal-4, and Tolerable-5 (and/or Agreeable, Satisfactory, Adequate, Marginal, and Tolerable) are referred to collectively as Acceptable.

Because each level of Acceptability (from 1 to 5) has a progressively higher threshold of acceptable negative side effect, notably ALA burn, each level of Acceptability also allows a higher ALA release rate, and therefore typically a higher ALA concentration.

For example, selecting ALA release rates from application Ser. No. 15/050,462 for each level of Acceptability could result in the following: ALA release rates ranging between about 0.9 mg/min (low from Table 3) and 8 mg/min (high from Table 2) may be Agreeable-1; between about 1.8 mg/min and 16 mg/min may be Satisfactory-2; between about 1.8 mg/min and 24 mg/min may be Adequate-3; between about 3.6 mg/min and 56 mg/min may be Marginal-4; and between about 3.6 mg/min and 84 mg/min may be Tolerable-5. Note, additional Non-Salt-formulation ALA release rates may be selected from the section titled "Independent ALA Percentage" in this disclosure.

The above ALA release rates would be expected to increase without an increase in the ALA burn when an effective, sufficient, desired, and/or specified amount of NaCl (or other salt) is incorporated into the formulation. For example, if such Salt-formulation ALA increase is found to be 50% greater than the Non-Salt-formulation ALA release rates, then the corresponding Levels of Acceptability would increase as follows: between about 1.35 mg/min and 12 mg/min may be Agreeable-1; between about 2.7 mg/min and 24 mg/min may be Satisfactory-2; between about 2.7 mg/min and 36 mg/min may be Adequate-3; between about 5.4 mg/min and 84 mg/min may be Marginal-4; and between about 5.4 mg/min and 126 mg/min may be Tolerable-5.

This shows, that while the section of this disclosure titled "Increased ALA" is initially directed to an increase in a formulation's ALA, it may also be applied to a formulation's ALA release rates. Therefore, a range of increase rates from the section titled "Increased ALA" may be applied in similar fashion to the 50% increase (of Salt-formulation ALA release rate compared to Non-Salt-formulation ALA release rate) disclosed in the preceding paragraph. For example, an increase ranging between about 20% and 50% (from the "Increased ALA" section), would include the 50% increase example of the preceding paragraph, but also a figure of 20% could be used or some other number in between such as 25%. If 25% is used, all of the "mg/min" numbers in the preceding paragraph would have the amount of increase of their values cut in half (compared to the 50% increase example). For example, a 25% increase would mean, "between about 2.7 mg/min and 36 mg/min may be Adequate-3" would increase by 0.675 and 9 respectively becoming "between about 3.375 mg/min and 45 mg/min may be Adequate-3". Note the change in decimal precision from 2.7 to 3.375 is not necessarily intended to be more precise than the initial precision. Therefore, 3.375 may be rounded to 3.4. This same principle of not increasing precision may be applied to any other number(s) in this disclosure and/or in application Ser. No. 15/050,462, specifically those from Tables 2 and 3. Additionally, any decimal fractions may be interpreted as (rounded to) full integers. Therefore, 3.4 may be rounded to 3.

The same range of ALA release rates from the section titled "Increased ALA" may also be used to create a reverse method; decreasing instead of increasing rates. That is, instead of increased rates, a given Salt-formulation ALA release rate (or range) could be decreased by an appropriate and/or reciprocal percentage to arrive at a Non-Salt-formulation ALA release rate. Note, the above example of 50% increase in ALA release rate from Non-Salt to Salt-formulation may be accomplished by multiplying by 1.5. Using the reverse method, the rate may be divided by 1.5 (reciprocal release rate 33.3%) to decrease the ALA release rate from Salt-formulation to Non-Salt-formulation. One such example being the Adequate-3 Salt-formulation ALA range of about 2.7 mg/min and 36 mg/min (from the above paragraph) becomes a Non-Salt-formulation ALA range between about 1.8 mg/min and 24 mg/min.

Note, increases in each Acceptability level may not be the same as, or proportionate to, the other levels. For example, the increase from Non-Salt-formulation to Salt-formulation might be 50% for the level Adequate-3, but 60% for the level Marginal-4 or 90% for Tolerable-5, and so on. Thus the range of ALA release rates from the section titled "Increased ALA" may be applied on an individual basis to each Acceptability level rather than applying uniformly to all of the Acceptability levels.

The question arises, how to establish ALA release rates (and/or ALA formulation concentrations and/or formulation dissolve rates) for the five progressive levels of Acceptability). A related question is how to compare such rates and/or concentrations to other, potentially infringing, formulations.

Because there are five levels of Acceptability and each of those has two sublevels, the total of these levels may be thought of, or utilized, as 10 levels along a continuum from 0 to 10. Therefore Acceptable-1 may be thought of as an alternate label for, or equivalent to, Level-1a; Acceptable-2 equivalent to Level-1b; Acceptable-3 equivalent to Level-2a; Acceptable-4 equivalent to Level-2b; Acceptable-5 equivalent to Level-3a; Acceptable-6 equivalent to Level-3b; Acceptable-7 equivalent to Level-4a; Acceptable-8 equivalent to Level-4b; Acceptable-9 equivalent to Level-5a; Acceptable-10 equivalent to Level-5b.

Salt and Burn Reduction

It is surmised that the advantageous properties of Na—R-ALA (including the reduced ALA burn) might extend to Na-ALA. It was not possible to find commercially available Na-ALA salt made from racemic ALA and therefore this hypothesis has not been tested. However, it was decided to pursue the idea of adding salt, NaCl (sodium chloride), to the ALA tablet formulation with the idea that it might be possible to create Na-ALA in the mouth's saliva during the tablet's dissolution, or create effects similar to an Na-ALA. This was also pursued in order to compare how much ALA burn reduction could be achieved by changing the formulation pH as opposed to making salt ions available or some other non-pH mechanism for ALA burn reduction.

To clarify, because the Na-ALA (or commercially available Na—R-ALA) may disassociate in solution, the positive effects from combining NaCl with ALA may not be due to the creation of Na-ALA molecules per se, but rather a solution of Na and ALA similar to what would be found if Na-ALA had been dissolved into solution, i.e., having similar "in-solution properties". Another way to think about this is that the superior properties of Na—R-ALA, or NaCl formulated with ALA, may have a common denominator the presence of the cation Na (or Na+). The common denominator the same cation may be more important than which form the cation is found in, bonded to either the anion R-ALA or chlorides.

It should also be noted that the degree an Na-ALA salt may be created, or something with properties similar to it, doesn't have to be 100% effective to be useful. For example, when a salt (such as NaCl) is included in the formulation, if only half of the ALA became a Na-ALA (or half the similar in-solution properties) then the reduction of the ALA burn might be somewhat similar to making a formulation of 50% ALA and 50% Na-ALA. And if salt in the formulation is even less effective at reducing the ALA burn, it might be somewhat similar to making a formulation of 75% ALA and 25% Na-ALA, and so on.

1) Na-ALA Equivalence

Therefore, a way to think about the addition of NaCl or another salt to a racemic ALA formulation is to measure the effect and/or benefit relative to racemic Na-ALA. The formulation may provide a benefit similar to a mixed ratio of about 50% Na-ALA to 50% ALA, about 75% Na-ALA to 25% ALA, or about 25% Na-ALA to 75% ALA The paired ratios must add up to 100%, so it is only necessary to specify the ratio of Na-ALA, because the ALA is automatically the remaining ratio. Therefore, the above could be specified as about 50%, 75%, or 25% Na-ALA. In these percentages, we consider 25% Na-ALA a more likely candidate, but 50% is preferable and 75% is more preferable. Because it is hard to be completely precise, these ratios would be more meaningfully expressed to include a range. Accordingly, the 50%, 75%, or 25% ratios could be specified as including ranges of plus or minus 5% (±5%), ±10%, ±15%, or ±20%. For example, 50%±10% meaning between 40% and 60% Na-ALA, and 50%±20% meaning between 30% and 70% Na-ALA.

Also, it may be experientially, experimentally or otherwise determined that alternative, and/or additional, ratios may be more applicable or accurate. Otherwise defined (and/or applied) in a similar fashion to the formulation Na-ALA percentages previously disclosed in this section, these alternative and/or additional, ratios could include 90%, 80%, 70%, 60%, 40%, 30%, 20%, or 10% Na-ALA. These ratios may be specified as including ranges of ±5%, ±10%, ±15%, ±20%, #25%, #30%, #40%, ±45%, ±50%, ±60%, ±75%, ±100%, ≤150%, 200%, ±300%, ±400% or #500% Na-ALA, except where the range goes beyond 0% or 100%. For example, selecting 40% from the Na-ALA ratios and 20% from the plus or minus ranges would be equivalent to specifying an Na-ALA ratio range of between 20% to 60% Na-ALA or selecting 10% from the Na-ALA ratios and 20% from the plus or minus ranges would be equivalent to specifying an Na-ALA ratio range of between-10% and 30% Na-ALA. In the instances when such specification results in range endpoints being 0% or less, or 100% or more, then such endpoints will be taken to mean about 1% or about 99% respectively. Therefore between −10% and 30% Na-ALA, becomes 1% and 30% Na-ALA.

Not having commercially available Na-ALA (racemic) makes this difficult to measure, therefore the above paragraphs in this section could read as replacing Na-ALA with any salt ion (cation) instead of the sodium (Na) and/or any ALA instead of the racemic ALA, i.e., another Alt-ALA. For example, a Salt-ALA, such as K-ALA, or Na—R-ALA in substitution of the Na-ALA. Different Alt-ALA ratios may be chosen for a given salt, ion source and/or Alt-ALA, as may be experientially, experimentally, or otherwise determined.

One working molecular hypothesis to explain the effect of salt on ALA burn is that the salt may be acting to mask the ALA burn rather than change the fundamental chemistry. Also, the reduction of ALA burn could be due to the presence of salt reducing the oral tissues' absorption of ALA, salt increasing the rate ALA transmission through the oral mucosa, or both. Note, it is well documented that cellular membrane and protein receptor dynamics are salt sensitive, such that membrane fluidity and receptor uptake is altered by various salt concentrations. Taste bud dynamics are also documented to change based upon various salt concentrations. These effects may underlie the diminished ALA burn rather than a direct effect of sodium upon ALA target binding.

By whatever mechanism, it was determined that the addition of NaCl to the formulation reduces the ALA burn during oral dissolution. That is, two ALA tablets, both having the same percentage of ALA and similar dissolution rates, but one tablet having NaCl added to the formulation ("NaCl-tablet") will cause that NaCl-tablet to have less of an ALA burn than the other tablet ("Non-Salt-tablet") which does not have NaCl added to it. Such NaCl-tablet and Non-Salt-tablet formulations being referred to as "NaCl-formulations" and "Non-Salt-formulation" respectively. The term "Salt-tablet" and "Salt-formulation" may be used, respectively, to include NaCl-tablet, NaCl-formulation, and other salt (i.e. potassium chloride) variations of tablets and formulations (for example, KCl-tablet).

2) Burn Reduction

One way to specify or measure the difference resulting from the addition of any organic or inorganic salt (such as NaCl) to a formulation, is to measure the degree to which the Salt-formulation has less of an ALA burn than the Non-Salt-formulation when dissolved in the mouth.

The reduction of ALA burn, when an effective, sufficient, desired, and/or specified, amount of a given salt is incorporated into the formulation could range between about 1% and 25%, preferably between about 20% and 50%, more preferably between about 40% and 75%, and most preferably between about 60% and 95% less burn than when the formulation has no salt (where 100% would mean no ALA burn at all). Note, the above ranges overlap and therefore may be combined into larger ranges such as a range between 20% and 75%, or a range between 1% and 95% ALA burn reduction.

However, it may be experientially, experimentally, or otherwise determined that alternative, and/or additional, ranges may be more applicable, effective, preferable, and/or Acceptable. Otherwise defined (and/or applied) in a similar fashion to the Salt-formulation burn reduction ranges previously disclosed in this section, these alternative, and/or additional, burn reduction ranges may be specified by selecting one number from a group of low range numbers and selecting one number from a group of high range numbers: the low range number group comprising about 1%, 3%, 5%, 7%, 10%, 15%, 20%, 25%, 30%, 40%, and 50%; and the high range number group comprising about 10%, 15%, 20%, 25%, 30%, 40%, 50%, 60%, 70%, 75%, 80%, 90% and 99%. For example, selecting 10% from the low range group and 40% from the high range group would be equivalent to specifying an ALA burn reduction range between 10% and 40% when a specified amount of salt is incorporated into the formulation or selecting 5% from the low range group and 60% from the high range group would be equivalent to specifying an ALA burn reduction range between 5% and 60% when a specified amount of salt is incorporated into the formulation.

In the above ranges of reduced ALA burn, 100% means that there is no burn at all, 0% means there has been no reduction of ALA burn, and 50% means the amount of ALA burn has been cut in half.

3) Increased ALA

Another simple and practical way to measure/specify the reduction of ALA burn, is to specify the increased percentage of ALA that may be incorporated into a Salt-formulation (including NaCl-formulation) while maintaining a similar, or equivalent, ALA burn to a Non-Salt-formulation. That is, increase the ALA concentration without increasing the ALA burn. This assumes both the Salt-formulation and the Non-Salt-formulation have similar dissolution rates and are of generally similar composition (except for changes in excipients or excipient ratios to overcome any effect that the salt has on dissolution rate, such that both have similar dissolution rates).

The additional concentrations of ALA that may be added to the formulation without an increase in ALA burn ("ALA-Addition") when an effective, sufficient, desired, and/or specified, amount of a given salt is incorporated into the formulation could range between about 1% and 25%, preferably between about 20% and 50%, more preferably between about 35% and 100%, and most preferably between about 75% to 200% more ALA than when the formulation comprises no salt. Our current experience would indicate a formulation with salt ranging between 25% and 100% increase of ALA, without additional ALA burn, is more likely a practical range. Note, the above ALA-Addition ranges overlap and therefore may be combined into larger ranges such as a range between 20% and 100% or a range between 1% and 200%.

However, it may be experientially, experimentally or otherwise determined that alternative, and/or additional, ALA-Addition ranges may be more applicable, effective, preferable, and/or Acceptable. Otherwise defined (and/or applied) in a similar fashion to the Salt-formulation ALA-Addition ranges previously disclosed in this section, these alternative, and/or additional, ALA-Addition ranges may be specified by selecting one number from a group of low range numbers and selecting one number from a group of high range numbers: the low range number group comprising about 0.5%, 1%, 2%, 3%, 4%, 5%, 6%, 7%, 8%, 9%, 10%, 12%, 15%, 20%, 25%, 30%, 40%, 50%, 75%, and 100%; and the high range number group comprising about 10%, 12%, 15%, 20%, 25%, 30%, 40%, 50%, 60%, 70%, 80%, 90%, 100%, 125%, 150%, 175%, 200%, 250%, 300%, 350%, 400%, 450%, 500%, 600%, 700%, 800%, and 900%. For example, selecting 40% from the low range group and 300% from the high range group would be equivalent to specifying a Salt-formulation ALA-Addition range between 40% and 300% when a specified amount of salt is incorporated into the formulation or selecting 100% from the low range group and 400% from the high range group would be equivalent to specifying an ALA burn reduction range between 100% and 400% when a specified amount of salt is incorporated into the formulation.

In a further example, if a formulation without salt has 4% ALA and has a similar ALA burn to a formulation with an effective amount of a given salt (such as NaCl) that has 6% ALA, then the Salt-formulation version has 50% more ALA than the Non-Salt formulation. And therefore, the utility provided is that the salt in the formulation has allowed a 50% increase in ALA without adverse ALA burn. If a 6% ALA formulation with salt had an ALA burn similar to a 3% ALA formulation without salt, then the salt has allowed the formulation to contain 100% more ALA than the non-salt version. If a formulation with 15% ALA and salt had an ALA burn similar to a 5% ALA formulation without salt, then the salt has allowed the formulation to contain 300% more ALA than the non-salt version.

4) Salt Percentage

The percentage of a given salt that is desired, required or is optimal to reduce the ALA burn in a given formulation depends on several factors. One factor is the salt itself. One salt may be more effective than another and therefore a higher percentage of the less effective salt might be required to get the same effect in a comparable formulation. Another factor is the percentage of ALA in the formula, generally the higher the ALA percentage in the formulation the higher percentage of a salt required or is optimal to reduce the ALA burn, however the ratio between the two is not necessarily linear. Determining the amount of salt that is effective is largely by trial-and-error experimentation.

A percentage of a given salt in a formulation for effectively or optimally reducing ALA burn may range between about 4% and 15%, preferably between about 3% and 10%, more preferably between about 1% and 8%, and most preferably between about 0.25% and 2%. The above ALA-Addition ranges overlap and therefore may be combined into larger ranges such as a range between 0.25% and 15% or a range between 1% and 10%.

However, it may be experientially, experimentally or otherwise determined that alternative, and/or additional, ranges of salt concentration in a Salt-formulation may be more applicable, effective, preferable, and/or optimal. Otherwise defined (and/or applied) in a similar fashion to the Salt-formulation salt ranges previously disclosed in this section, these alternative, and/or additional, salt ranges may be specified by selecting one number from a group of low range numbers and selecting one number from a group of high range numbers: the low range number group comprising about 0.25%, 0.5%, 1%, 2%, 3%, 4%, 5%, 7%, 10%, 12% and 15%; and the high range number group comprising about 2%, 3%, 4%, 5%, 6%, 7%, 8%, 9%, 10%, 12%, 15%, 20%, 25%, 30%, 35%, 40%, 45%, and 50%, For example, selecting 0.5% from the low range group and 12% from the high range group would be equivalent to specifying a Salt-formulation salt concentration range between 0.5% and 12% or selecting 4% from the low range group and 7% from the high range group would be equivalent to specifying a Salt-formulation range between 4% and 7% ALA.

5) Independent ALA Percentage

Another way to specify concentrations of formulation ALA is to do it independently of any reference to Non-Salt-formulations. As such, ALA concentrations in a Salt-formulations when an effective, sufficient, desired and/or specified amount of salt (such as NaCl) is in the formulation, could range between about 1% and 6%, preferably between about 2% and 10%, more preferably between about 3% and 15%, and most preferably between about 5% and 25% ALA. Note, the above ranges overlap and therefore may be combined into larger ranges such as a range between 2% and 15% or a range between 1% and 25% ALA in the Salt-formulation.

However, it may be experientially, experimentally or otherwise determined that alternative, and/or additional, ranges of ALA concentration in a Salt-formulation may be more applicable, effective, preferable, and/or Acceptable. Otherwise defined (and/or applied) in a similar fashion to the Salt-formulation ALA ranges previously disclosed in this section, these alternative, and/or additional, ALA ranges may be specified by selecting one number from a group of low range numbers and selecting one number from a group of high range numbers: the low range number group comprising about 0.25%, 0.5%, 1%, 2%, 3%, 4%, 5%, 7%, 10%, 12% and 15%; and the high range number group comprising about 6%, 7%, 8%, 9%, 10%, 12%, 15%, 20%, 25%, 30%, 35%, 40%, 45%, and 50%. For example, selecting 0.5% from the low range group and 12% from the high range group would be equivalent to specifying a Salt-formulation ALA concentration range between 0.5% and 12% or selecting 4% from the low range group and 35% from the high range group would be equivalent to specifying a Salt-formulation range between 4% and 35% ALA.

There are many forms of salts besides NaCl that may provide either sodium or other suitable ions (cations) to act in a somewhat similar manner to NaCl (for example KCl). Even if they are not as effective, they may still have some effect. For simplicity's sake they could be chosen from the same ranges sets as the NaCl, but probably or possibly with different ranges being chosen which are more appropriate for the selected salt or ion source as may be experientially, experimentally or otherwise determined. The range sets being referred include the previous section titled "Na—R-ALA and Salt-ALA" and the four sections that are subsets of the "Salt and Burn Reduction" section: "(1) Na-ALA Equivalence", "(2) Burn Reduction", "(3) Increased ALA", "(4) Salt Percentage" and this section "(5) Independent ALA Percentage".

TABLE 1

In situ Oral Dissolution Trial Results (3.43 g Avg, 3% ALA, hard candy sugar lozenge)

| Time (min) | Weight (g) | Change Weight (g) | % ALA | mg ALA lost | mg ALA in Solution | Release Rate (mg/min) |
|---|---|---|---|---|---|---|
| 0 | 3.43 | 0 | 3 | 0 | 0.00 | 0.00 |
| 1 | 3.43 | 0.59 | 3 | 17.63 | 17.63 | 17.63 |
| 2 | 2.84 | 0.67 | 3 | 20.18 | 37.80 | 20.18 |
| 3 | 2.17 | 0.55 | 3 | 16.58 | 54.38 | 16.58 |
| 4 | 1.62 | 0.49 | 3 | 14.70 | 69.08 | 14.70 |
| 5 | 1.13 | 0.46 | 3 | 13.65 | 82.73 | 13.65 |
| 6 | 0.67 | 0.32 | 3 | 9.53 | 92.25 | 9.53 |
| 7 | 0.36 | 0.21 | 3 | 6.15 | 98.40 | 6.15 |
| 8 | 0.15 | 0.10 | 3 | 3.08 | 101.48 | 3.08 |
| 9 | 0.05 | 0.05 | 3 | 1.43 | 102.90 | 1.43 |

While the ALA concentration levels disclosed in this section (titled: Independent ALA Percentage) are initially intended to define Salt-formulations, they may also be used to define Non-Salt-formulations.

All else being equal between two formulations (such as tablets), the formulation with a higher concentration of ALA will release more ALA at any given time and release more ALA on an average. For oral dissolution, this will result in a higher concentration of ALA in the saliva and on the oral mucosa, which in turn will result in a greater burn effect. Therefore, the concentration of ALA is the simplest method for measuring/specifying a formulation's relationship to the resulting concentration of ALA in the saliva and the resulting burn effect during oral dissolution. Because the difference between formulations may not be that significant, the concentration of ALA in the formulation may be a good approximation of the concentration of ALA released.

Contrary to that generalization, two formulations (tablets, lozenges, troches and/or etc.) may have the same concentration of ALA, but have two different dissolution rates (due to formulation, manufacturing methods, or shape/surface area). This will result in two different amounts of ALA in the saliva and result in two different levels of burn effect.

Therefore, a good method of measuring or specifying a formulation's relationship to its resulting burn effect upon oral dissolution is the measure and/or specification of the amount of ALA released into the saliva over a given time period. The simple way to do this is to measure the rate at which a formulation dissolves in the mouth and correlate that with (multiplied by) the formulation's ALA concentration.

To be more precise and descriptive, a way to specify ALA tablet release rates ("C") during dissolution is to describe it as the result of multiplying its two components by each other. Those two components being: (A) tablet weight loss per unit time, and (B) percent ALA concentration. An example of these components may be seen in the previously mentioned TABLE 1 of the incorporated Ser. No. 15/050,462 Application and shown below. Its third column shows the lozenge weight loss per unit time as: "Change Weight (g)", in this instance, grams per minute. The fourth column contains the formulation's percent ALA concentration as: "% ALA Tablet". The entries of these two columns are multiplied by each other providing the results in column seven, the ALA release rate labeled: "Release Rate (mg/min)".

Taking one of the many previous disclosures of ALA concentration percentages (B) and multiplying it by weight loss (formulation dissolved) per unit time (A) will disclose an ALA release rate (C). Simply, A×B=C.

This method is used in the incorporated CIP application Ser. No. (Ser. No. 15/050,462). The results are given in TABLE 1: "In situ Oral Dissolution Trial Results". The 3% ALA lozenge tested was found to have a peak ALA Release Rate of 20.2 mg/min and an average ALA Release Rate of 11.4 g/min. For the Oral Dissolution Trial Peak ALA Release Rate of 20 mg/min was found to be acceptable, 40 mg/min was neutral, and 60 mg/min was unacceptable. Mg/min being milligrams of ALA released during dissolution per minute.

Extrapolating from TABLE 1, the acceptable ALA release rates and ranges of an ALA tablet might be expected to have a Peak ALA Release Rate/min ranging between about 10 mg/min and 30 mg/min (20 mg/min±10 mg/min), between about 30 mg/min and 50 mg/min for neutral, and between about 50 mg/min and 70 mg/min would be expected to be unacceptable. Combining the acceptable and neutral ranges would make a range between about 10 mg/min and 50 mg/min which could be termed Adequate. The ranges with the low end of 10 mg/min could be lower, such as 5 mg/min, 2 mg/min or even 1 mg/min, because the small amounts should not cause a strong ALA burn, however it would have to be determined which of these lower rates could still provide a reasonable, noticeable, prophylactic, or effective dose of ALA without making the ALA tablet overly large for oral dissolution.

Because the ALA tablet has less ALA polymerization which makes it more potent than an equivalent ALA lozenge, and the ALA tablet typically has less mass than the hard candy ALA lozenge, it may be that lower ALA release rate ranges may be appropriate, functional, acceptable and/or desirable for the ALA tablet.

For example, the ALA tablet's Peak ALA Release Rate/min could range between about 1 mg/min and 8 mg/min, preferably between about 5 mg/min and 25 mg/min, more preferably between about 10 mg/min and 50 mg/min, and most preferably between about 20 mg/min and 90 mg/min. Note, the above ranges overlap and therefore may be combined into a larger range such as a range between about 5 mg/min and 50 mg/min or a range between about 1 and 90 mg/min of ALA released.

However, it may be experientially, experimentally or otherwise determined that alternative, and/or additional, Peak ALA Release Rate/min ranges may be more applicable, effective, preferable, and/or Acceptable. Otherwise defined (and/or applied) in a similar fashion to the Peak ALA Release Rates/min previously disclosed in this section, these alternative, and/or additional, Peak ALA Release Rate/min ranges may be specified by selecting one number from a group of low range numbers and selecting one number from a group of high range numbers: the low range number group comprising about 1, 2, 3, 4, 5, 6, 7, 8, 9, 10, 12, 15, 17, 20, and 25 mg/min of ALA released; and the high range number group comprising about 8, 9, 10, 12, 15, 18, 20, 25, 30, 40, 50, 60, 70, 80, 90, 100, 110, 120, 130, 140, 150, 175, and 200 mg/min of ALA released. For example, selecting 5 mg/min from the low range group and 70 mg/min from the high range group would be equivalent to specifying a Peak ALA Release Rate/min range between 5 and 70 mg/min; or selecting 2 mg/min from the low range group and 175 mg/min from the high range group would be equivalent to specifying a Peak ALA Release Rate/min range between 5 and 175 mg/min of ALA released.

The Peak ALA Release Rate is important because that is when the maximum ALA concentration in the saliva will occur and therefore the greatest problem with undesirable side effects including ALA burn. Still, the cumulative effect of high ALA concentrations in the saliva will also impact the ALA burn. Therefore, specifying an Average ALA Release Rate/min is another way to control the ALA exposure of the oral tissues during the dissolution of the formulation.

The Average ALA Release Rate/min may range between about 0.5 mg/min and 4 mg/min, preferably between about 2 mg/min and 12 mg/min, more preferably between about 5 mg/min and 25 mg/min, and most preferably between about 10 mg/min and 45 mg/min. Note, the above ranges overlap and therefore may be combined into a larger range such as a range between about 2 mg/min and 25 mg/min or a range between about 0.5 and 45 mg/min of ALA released.

However, it may be experientially, experimentally, or otherwise determined that alternative, and/or additional, Average ALA Release Rate/min ranges may be more applicable, effective, preferable, and/or Acceptable. Otherwise defined (and/or applied) in a similar fashion to the Average ALA Release Rates/min previously disclosed in this section, these alternative, and/or additional, Average ALA Release Rate/min ranges may be specified by selecting one number from a group of low range numbers and selecting one number from a group of high range numbers: the low range number group comprising about 0.25, 0.5, 2, 3, 4, 5, 6, 7, 8, 9, 10, 12, 15, 17, and 20 mg/min of ALA released; and the high range number group comprising about 8, 9, 10, 12, 15, 18, 20, 25, 30, 40, 50, 60, 70, 80, 90, 100, 110, 120, 130, 140, and 150 mg/min of ALA released. For example, selecting 5 mg/min from the low range group and 50 mg/min from the high range group would be equivalent to specifying an Average ALA Release Rate/min range between 5 and 50 mg/min; or selecting 2 mg/min from the low range group and 140 mg/min from the high range group would be equivalent to specifying an Average ALA Release Rate/min range between 2 and 140 mg/min of ALA released.

Given a particular or selected ALA concentration in the formulation then the ALA release rate is dependent on the dissolution rate of the formulation, Therefore, specifying the weight loss of the formulation during the time of its dissolution will specify the ALA release rate. Accordingly, we disclose a variety of ALA release rates by disclosing a variety of weight losses per unit time (B), as follows.

A range of ALA release rates (C) is provided as the result of multiplying one of a previously disclosed range of ALA concentration percentages (B) multiplied by one of the following range of weight losses per unit time (A). A formulation's (including tablet, lozenge, pill, or troche or the like) weight loss during dissolution (A) could range between about 5 mg/min and 25 mg/min, preferably between about 10 mg/min and 75 mg/min, more preferably between about 50 mg/min and 150 mg/min, and most preferably between about 100 mg/min and 1000 mg/min. Note, the above ranges overlap and therefore may be combined into larger ranges such as a range between 10 mg/min and 150 mg/min or a range between 5 mg/min and 1000 mg/min of formulation weight loss during dissolution (i.e. formulation dissolved).

However, it may be experientially, experimentally, or otherwise determined that alternative, and/or additional, ranges may be more applicable, effective, preferable, and/or Acceptable. Otherwise defined (and/or applied) in a similar fashion to the formulation weight losses previously disclosed in this section, these alternative, and/or additional, ranges of formulation weight loss during dissolution may be specified by selecting one number from a group of low range numbers and selecting one number from a group of high range numbers: the low range number group comprising about 1, 3, 5, 7, 10, 12, 15, 17, 20, 22, 25, 30, 35, 40, 45, 50, 60, 70, 80, 90, 100, 125, 150, 175 and 200 mg/min; and the high range number group comprising about 10, 15, 20, 25, 30, 40, 50, 60, 70, 80, 90, 100, 125, 150, 175, 200, 225, 250, 275, 300, 350, 400, 450, 500, 600, 700, 800, 900, 1000, 1100, 1200, 1300, 1400, and 1500 mg/min. For example, selecting 12 mg/min from the low range group and 90 from the high range group would be equivalent to specifying a range of formulation dissolved (weight loss per minute) between about 12 and 90 mg/min while selecting 50 mg/min from the low range group and 1200 mg/min from the high range group would be equivalent to specifying a range of formulation dissolved between at about 50 and 1200 mg/min.

The above formulation weight loss ranges may be selected for defining the average mg/min (weight loss per minute) or peak mg/min.

The ALA release rate(s) may be measured in vivo or in situ as outlined in the Ser. No. 15/050,462 Application.

Establishing Levels of Acceptability

One method of testing to establish such rates and/or concentrations would be to (1) provide 12, or more, test subjects with formulations that have a range of ALA release rates. Note, the formulations with the lower ALA release rates (and/or concentrations) should be taken first to minimize the side effects between ALA formulations. If the accumulation of side effects appears to be skewing the data, then appropriate waiting times between taking different formulations should be instituted. (2) Provide the subjects with a questionnaire that asks them to determine which ALA release rate is appropriate for each level of Acceptability. (3) Use the average of such questionnaire results to determine the best match between each level of Acceptability and the appropriate ALA release rate. This may be called a First Acceptability Study. The same method could then be used to compare claimed formulations with other formulations.

A Second Acceptability Study method would be the same as the First Acceptability Study method, but the number of test subjects required would be increased until the results of the overall study were statistically significant or the results for each Acceptability level were statistically significant. The same method could be used to compare claimed formulations with other formulations.

An alternate method(s) of performing a Third Acceptability Study, as yet undefined, may be used. In that instance, the comparison testing (claimed formulations vs other formulations) would use such alternate testing methodology as was used to establish the ranges for claimed formulations.

Other salts besides NaCl may provide an alternative sodium or other ion source. These alternative salts may assist in forming an ALA salt or may be included in the ALA tablet formulation as a separate ingredient from ALA. One or more of these alternative salts may be effective in reducing ALA burn or improve ALA transmission from the mouth to the bloodstream. These alternative salts may include the salts listed below.

Other neutral salts (also known as normal salts) including; Na2SO4 (sodium sulfate) and CH3COONa (sodium acetate);

Acidic or basic salts may be alternative salts, as long as they're not too strongly acidic or basic.

Mineral salts that contain metals including sodium, calcium, ammonium phosphate, potassium (including KCl), magnesium, chlorine, sulfur, and phosphorus may be used.

Organic, inorganic, monatomic, polyatomic, double, mixed, and complex salts may be used.

The inorganic salts including Potassium sulfate, Potassium nitrate, Potassium chloride, Potassium carbonate, Potassium bicarbonate, Sodium sulfate, Sodium nitrate, Sodium chloride; the cations of inorganic salts including: Na+, K+, Ca2+, Mg2+, Fe2+, Fe3+,Cu+, Cu2+, Mn2+, Mn4+, Co2+, Cr3+, Cr6+, Cd2+, Zn2+; the anions of inorganic salts including: Cl−, (HCO3)−, (HPO4)2−, Br−, I−; and the inorganic salts that are combination of one of the above cations and one of the above anions.

The organic salts including: monosodium glutamate, the phosphinates, the hydrazinium salts, the urates, the diazonium salts, the salts of cocaine, the oxalate salts, the bechgaard salts, methoxide, the tartrates, the iminium salts, trolamine salicylate, aluminium (also known as aluminum) monostearate, triphenylmethyl hexafluorophosphate, the organophosphates, choline chloride, copper ibuprofenate, mellite, tetrapropylammonium perruthenate, and the sorbates.

Different salts may also be used in combination; including sodium chloride, potassium chloride calcium carbonate, sodium acetate sodium bicarbonate, or potassium bicarbonate; to offset negative side effects, control pH, control taste or interactively improve performance.

Note, in evaluating the salts alternatives one should consider not only their effectiveness in reducing ALA burn, but also their taste. Additional considerations include changes in texture, manufacturability, and dissolution rate.

NaCl, and most salts, tends to dissolve fairly rapidly and therefore may speed up an ALA tablet's dissolution rate. Therefore, the tablet formulation may be altered to counteract that tendency and provide the desired dissolution rate.

Also, due to its slightly effervescence effect, the bicarbonate appears to assist in spreading the ALA more rapidly into the saliva and therefore creating less of a "hot spot" area of high ALA concentration in the oral tissues directly adjacent to the tablet.

On the other hand, the effervescence could be a negative quality because the ALA cannot be sequestered in a given region of the mouth as effectively, such as under the tongue or buccally, which are areas known to have a higher rate of active ingredient migration across the oral membrane and into bloodstream. Also, such sequestering may reduce ALA contact with the top of the tongue and thereby reduce any taste or irritability problems there.

To refer collectively to the group of organic and/or inorganic salts that may assist in reducing the ALA burn, we may refer to them as Burn Reduction Salts or BR Salts. The amount of a given BR Salt depends, in part on the percentage of ALA used in the formulation. The ratio of BR Salt to ALA may vary somewhat depending on the particular ingredient used, but may be in a BR Salt to ALA range between about 5% and 25%, preferably between about 20% and 75%, more preferably between about 50% and 100%, and most preferably between about 75% and 200%, (where 100% means the BR Salt and ALA weights are the same). For example, 1 g of BR Salt and 2 g of ALA in a formulation would mean the BR is 50% of the weight of the ALA and therefore falls within the middle two of four of the ranges disclosed above in this paragraph, while, 2 g of BR Salt and 2 g of ALA in a formulation would mean the BR is 100% of the weight of the ALA and therefore falls within the last two ranges disclosed in this paragraph, Because the above ranges overlap, they may be combined into larger ranges such as a range between 20% and 100% or a range between 5% and 200% BR Salt to ALA.

However, it may be experientially, experimentally, or otherwise determined that alternative, and/or additional, ranges of BR Salt to ALA may be more applicable or preferable. Otherwise defined (and/or applied) in a similar fashion to the BR Salt ranges previously disclosed in this section, these alternative, and/or additional, BR Salt to ALA ranges may be specified by selecting one number from a group of low range numbers and selecting one number from a group of high range numbers: the low range number group comprising about 1%, 2%, 5%, 10%, 15% 20%, 25%, 30%, 35%, 40%, 45%, 50%, 55%, 60%, 65%, 70%, and 75%; and the high range number group comprising 30%, 35%, 40%, 45%, 50%, 55%, 60%, 65%, 70%, 75%, 80%, 90%, 100%, 125%, 150%, 175%, 200%, 300%, 400%, and 500%. For example, selecting 30% from the low range group and 90% from the high range group would be equivalent to specifying a formulation with a BR Salt to ALA range between about 30% and 90%, or selecting 15% from the low range group and 125% from the high range group would be equivalent to specifying a range between about 15% and 125% BR Salt to ALA.

Because the ALA burn is not only a problem for the oral tissues, but also for the tissues of the G.I. tract the addition of a salt to the ALA formulation may be useful in reducing the ALA burn during ingestion. The amount of salt added as percentage of the formulation may be specified as disclosed in the "Salt Percentage" section. Alternatively, the percentage of salt relative to the amount of ALA added to a formulation may be specified as disclosed in the "Burn Reduction Salts & Ratios" section. The formulation includes the forms of tablet, lozenge, capsule, gel, gel cap, liquid and/or reconstituted liquid forms.

If the BR Salts help stabilize the ALA (by creating a salt-ALA), their addition mixed into the ALA powder before adding it to the molten hot candy matrix may reduce the amount of polymerization and possibly even sublimation.

That is to say, as the ALA is heated, the BR Salt may interact with the ALA and form an ALA salt, preventing or reducing polymerization. Therefore, the hard candy ALA lozenge may be able to achieve greater levels of ALA concentration similar to those disclosed above for the ALA compressed tablet.

Therefore, to make a BR Salt & ALA lozenge, a BR Salt is added to, and mixed together with, the ALA to form a powder mixture which we will call an API Mass. The API Mass is then added to the molten hot candy matrix.

Subsequently, the flavoring and optionally coloring are added. They are added as late as possible during the cooling of the hot candy matrix to minimize ALA sublimation.

The hot candy matrix ("first molten mass") is comprised of natural sugar(s) (sucrose, glucose, fructose and the like), corn syrup (or similar) and sometimes water; and/or comprised of a sugar substitute(s) (isomalt and the like) and usually water. Restated, the hot candy matrix comprises the majority of the candy matrix and contains everything necessary to create hard candy except for flavoring, coloring, and active ingredients. The hot candy matrix is raised to a temperature of around 300° F. (for sucrose) (or the approximately similar temperature as appropriate for the given natural or substitute sugar ingredients) to create a hard crack candy.

The formulas (or formulations) for the ALA compressed tablet comprise(s) the active ingredient ALA and other ingredients. Those other ingredients may include excipients (non-active ingredients) that assist in tablet manufacturing, shelf life, and/or durability; tablet dissolution, taste, texture, and/or appearance; ALA burn reduction; ALA bioavailability; and may include other active ingredients. The interaction of multiple ingredients means the addition of a single ingredient, or the adjustment of it, may require the adjustment of one or more other ingredients. The following are the ingredients including excipients and active ingredients may be used in an ALA formulation (including tablets, compressed tablets, lozenges, hard candy lozenges, troches, gummies, gums, gels, liquids, and/or a solid or gel that can be reconstituted into a liquid):

A single ingredient may assist in several of the above categories simultaneously. For example, sugar(s) is a major ingredient in the ALA tablet for several reasons: it improves ALA bioavailability, may act as a binder, a disintegrate, a filler and assists in flavor. Accordingly, a single ingredient may appear in multiple categories.

ALA active ingredients include: racemic ALA, R-ALA, S-ALA, Na—R-ALA, K—R-ALA, and other Salt-ALAs previously disclosed.

Non-ALA active ingredients include: vitamin B1, vitamin B6, vitamin B12, and other non-ALA active ingredients previously disclosed.

Assisting ingredients (not generally or typically considered active ingredients, but which have an effect on active ingredients, specifically reducing side effects, so could be considered secondarily active ingredients) include:

- salts and salt compounds including sodium chloride and those previously disclosed;
- sugars and sugar substitutes including sucrose (including Domino DiPac), dextrose, fructose, maltose, molasses powder, and isomalt and those previously disclosed; and
- Fuji Neusilin including Neusilin US2, UFL2 and S2.

Binders include:

- sugars and sugar substitutes including sucrose, DiPac, and those previously disclosed;
- copovidone, copolyvidone, crospovidone, and povidone (including BASF Kollidons such as Kollidon VA64, VA 64 Fine, CL-M and CL-SF);
- gums including, gum arabic, guar gum (including NutraTab® guar gum with tricalcium phosphate), tragacanth gum, acacia gum, locust bean gum, karaya gum, carrageenan, and xanthan gum;
- miscellaneous binders including, sodium carboxymethylcellulose, agar, microcrystalline cellulose, pregelatinized starch, ethylcellulose, methylcellulose, methylcellulose hydroxypropyl, poly(acrylic acid), dextrin, gelatin, glucose, alginic acid, molasses; and
- hydrogenated oil powder (including JRS Pharma Lubritab® and BASF Kolliwax® HCO).

Lubricants include:

- stearic acid (including BASF Kolliwax® S Fine), magnesium stearate, talc, glyceryl monostearate and;
- hydrogenated oil (including JRS Pharma Lubritab® and BASF Kolliwax HCO).

Disintegrants include:

- crospovidone (type A and type B) (including BASF Kollidons such as Kollidon CL, CL-F, CL-M and CL-SF);
- soy polysaccharides including JRS Emcosoy®; and
- corn and potato starches, pregelatinized starch, sodium starch glycolate, sodium carboxymethylcellulose (CMC), croscarmellose, microcrystalline cellulose, polyvinylpyrrolidone (PVP), cation-exchange resins, clays, magnesium aluminum silicate.

Fillers include sugars and sugar substitutes including those previously disclosed.

Texture Agents include: modified food starch, propylene glycol alginate, pectin; and gums such as gum arabic, guar gum (including Nutra Tab guar gum with tricalcium phosphate), tragacanth gum, acacia gum, locust bean gum, karaya gum, carrageenan, and xanthan gum.

Flavors include: cinnamon, ginger, licorice, rum, molasses, cherry, mint, and RebA (*Stevia* extract).

Glidants include: fumed silicon dioxide and talc. 10% ALA, and 5% Sodium Bicarbonate-Formulation Below is the V-14/F-5 formulation with 10% ALA, and 5% sodium bicarbonate (of Sep. 24, 2016). Abbreviations: Ginger is ginger flavoring powder, Tag Gum is Tragacanth Gum, Vit. B12 is vitamin B-12 diluted with dextrose to a 1% Concentration, Orange is powdered food coloring, API is 97.5% ALA combined and 2.5% Fuji's Neusilin US-2 mixed together before their addition to the rest of the formulation, DiPac is DiPac sugar, CL-SF is BASF Crospovidone CL-SF, and Baking Soda is sodium bicarbonate. The ingredients in Groups 1 and 2 are mixed separately, combined, and pressed into compressed tablets.

TABLE 2

| Group 1 (V-14) | | | | | | | | |
|---|---|---|---|---|---|---|---|---|
| Ginger | Tag Gum | Guar Gum | Vit. B12 | Orange | API | Red Color | DiPac | TOTAL |
| 15.00% | 3.00% | 2.00% | 0.20% | 0.30% | 10.26% | 0.40% | 18.84% | 50.0% |

TABLE 3

| Group 2 (F-5) | | | | | |
|---|---|---|---|---|---|
| CL-SF | Corn Starch | Stearic Acid | Baking Soda | DiPac | TOTAL |
| 4.00% | 2.00% | 1.20% | 5.00% | 37.80% | 50.0% |

10% ALA, 5% NaCl-Formulation

Below is the V-14/F-10 formulation with 10% ALA, and 5% NaCl (of Sep. 28, 2016). Abbreviations: Ginger is ginger flavoring powder, Tag Gum is Tragacanth Gum, Vit. B12* is vitamin B-12 diluted with dextrose to a 1% Concentration, Orange is powdered food coloring, API is 97.5% ALA combined and 2.5% Fuji's Neusilin US-2 mixed together before their addition to the rest of the formulation, DiPac is DiPac sugar, CL-SF is BASF Crospovidone CL-SF, and the NaCl* is pink Himalayan salt. The ingredients in Groups 1 and 2 are mixed separately, combined and pressed into compressed tablets. The tablets made are circular, approximately 9 mm in diameter, approximately 5 mm tall, have a weight of approximately 0.35 g.

TABLE 4

| Group 1 (V-14) | | | | | | | | |
|---|---|---|---|---|---|---|---|---|
| Ginger | Tag Gum | Guar Gum | Vit. B12* | Orange | API | Red Color | DiPac | TOTAL |
| 15.00% | 3.00% | 2.00% | 0.20% | 0.30% | 10.26% | 0.40% | 18.84% | 50.0% |

TABLE 5

| Group 2 (F-10) | | | | |
|---|---|---|---|---|
| CL-SF | Stearic Acid | NaCl* | DiPac | TOTAL |
| 4.00% | 1.20% | 5.00% | 39.80% | 50.0% |

10% ALA, 1 NaCl: 2 Na2Phos-Formulation

Below is the V/F-24 formulation with 10% ALA, 8% disodium phosphate, and 4% NaCl (of Oct. 7, 2016). Abbreviations: Lime is lime flavoring powder, Tag Gum is Tragacanth Gum, Vit. B-1* is vitamin B-1 diluted with dextrose to a 1% Concentration, API is 97.5% ALA combined and 2.5% Fuji's Neusilin US-2 mixed together before their addition to the rest of the formulation, DiPac is DiPac sugar, and CL-SF is BASF Crospovidone CL-SF. The ingredients in Groups 1 and 2 are mixed separately, combined and pressed into compressed tablets. The tablets made are circular, approximately 9 mm in diameter, approximately 5 mm tall, have a weight of approximately 0.35 g. and have a dissolution time of about 3-4 minutes.

TABLE 6

| Group 1 (V) | | | | | | | | | |
|---|---|---|---|---|---|---|---|---|---|
| Lime | Tag Gum | Guar Gum | Vit. B | Color | Di | API | NaCl | DiPac | TOTAL |
| 15.0% | 3.0% | 2.0% | 0.2% | 0.3% | 8.0% | 10.3% | 4.0% | 7.2% | 50.0% |

TABLE 7

| Group 2 (F-24) | | | | |
|---|---|---|---|---|
| CL-SF | Corn Starch | Stearic | DiPac | TOTAL |
| 4.0% | 8.0% | 1.2% | 36.8% | 50.0% |

Part of the purpose for including the disodium phosphate in the formulation is to reduce the acidity.

10% ALA, 5% Salt-Formulation

Below is the V-A/F-30 formulation with 10% ALA, 5% NaCl, and Molasses (of Nov. 12, 2016). Abbreviations: CL-SF is BASF Crospovidone CL-SF, Vit. B-1* is vitamin B-1 diluted with dextrose to a 1% Concentration, Tag Gum is Tragacanth Gum, DiPac is DiPac sugar, and Molasses is Molasses powder. The ingredients in Groups 1 and 2 are mixed separately, combined and pressed into compressed tablets. The ALA and NaCl in the Group 2 were mixed together before adding the molasses powder.

TABLE 8

| Group 1 (V-A) | | | | | | | | |
|---|---|---|---|---|---|---|---|---|
| CL-SF | Corn Starch | Stearic Acid | Vit B-1* | Tag Gum | Guar Gum | Color | Dextrose | DiPac |
| 6.0% | 6.0% | 1.2% | 0.2% | 3.0% | 2.0% | 0.2% | 15.0% | 16.4% |

TABLE 9

| Group 2 (F-30) | | |
|---|---|---|
| ALA | NaCl | Molasses |
| 10.0% | 5.0% | 35.0% |

5.5% ALA/NaCl Tablet Formulations 7021A and 7021B

STEPS (Formulation for lab and trial production runs)

1. Screen all materials before weighing. Please use a #20 mesh screen (i.e., opening of 0.85 mm or 0.033 inches).

2. ALA and Neuslin US-2 together and mix. Then add the sodium chloride and mix. Then add all the ingredients in the list below except flavor and DiPac and mix.

3. Mix the flavor and Dipac with each other to create a second mixture, and then add that second mixture to the first mixture.

4. Screen entire mixture with a #20 mesh screen.

5. For any lumps remaining above the #20 mesh screen, crush them with mortar and pestle until they can pass through screen.

6. Use formulation to make compressed tablets.

TABLE 10

| 5.5% ALA/Salt Direct Compression Tablet Formulation 7021A | |
|---|---|
| Ingredient | Percent |
| ALA | 5.5 |
| Neuslin US-2 | 0.26 |
| MIX ABOVE | |
| Tragacanth Gum | 3 |
| Guar Gum | 2 |
| Stearic Acid | 1.2 |

TABLE 10-continued

| 5.5% ALA/Salt Direct Compression Tablet Formulation 7021A | |
|---|---|
| Ingredient | Percent |
| GRS LubriTab (BF) | 6 |
| Kollidan VA-64 Binder | 4 |
| Calcium Carbonate | 5 |
| MIX ABOVE | |
| Mix DiPac and Flavor with each other first | |
| Flavor | 16 |
| DiPac Sugar | 52.04 |
| MIX ABOVE | |

TABLE 11

| 10% ALA/Salt Tablet Formulation 7021B | |
|---|---|
| Ingredient | Percent |
| ALA | 10 |
| Neusilin US-2 | 0.5 |
| MIX ABOVE | |
| Sodium Chloride | 10 |
| MIX ABOVE | |
| Tragacanth Gum | 3 |
| Guar Gum | 2 |
| Stearic Acid | 1.2 |
| GRS LubriTab (BF) | 6 |
| Kollidan VA-64 Binder | 4 |
| Calcium Carbonate | 5 |
| MIX ABOVE | |
| Mix DiPac and Flavor with each other first | |
| Flavor | 18 |
| DiPac Sugar | 40.3 |
| MIX ABOVE | |

5.5% ALA/NaCl/VitB Tablet Formulation 70110

Formulation for lab and trial production runs. Steps and instructions are similar to the above 7021A and 7021B formulations. Reminder: mix the flavor and Dipak sugar with each other to create a second mixture, and then add that second mixture to the first mixture (all the other previous ingredients in the list).

TABLE 12

| AlphaBon ™ Compression Tablet Formula (Jan. 10, 2017) | | | |
|---|---|---|---|
| Desired Ingredient List | | g Per Batch | |
| Desired % ALA | 5.5 | Amount ALA | 550 |
| Desired % Neusilin | 0.26 | Amount Neusilin | 26 |
| -- Mix -- | | | |
| Desired % Sodium Chloride | 5 | Amount Salt | 500 |
| -- Mix -- | | | |
| Desired % B1 | 0.075 | Amount B1 | 7.5 |
| Desired % B6 | 0.085 | Amount B6 | 8.5 |
| Desired % B12 | 0.001 | Amount B12 | 0.1 |
| -- Mix -- | | | |
| Desired % Tragacanth Gum | 3 | Amount Tag | 300 |
| Desired % Guar Gum | 2 | Amount Guar | 200 |
| Desired % Stearic Acid | 1.2 | Amount SA | 120 |
| Desired % GRS LubriTab ® (BF) | 6 | Amount BF | 600 |
| -- Mix -- | | | |
| Desired % Kollidan VA-64 Binder | 4 | Amount Binder | 400 |
| -- Mix -- | | | |
| Desired % Calcium Carbonate | 5 | Amount Ca Carbonate | 500 |

TABLE 12-continued

| AlphaBon ™ Compression Tablet Formula (Jan. 10, 2017) | | | |
|---|---|---|---|
| Desired Ingredient List | | g Per Batch | |
| -- Mix -- | | | |
| Desired % Flavor | 16 | Amount Flavor | 1600 |
| DiPac Sugar Matrix | | Amount Sugar | 5187.9 |
| Final Volume (grams) | 1000 | | |
| The Above Formula Should Give Tablets with the Following Active Ingredients: | | | |
| Tablet size (mg) | 2000 | 1000 | 750 |
| Amount ALA (mg) | 110 | 55 | 41.25 |
| Amount B1 (mg) | 1.5 | 0.75 | 0.5625 |
| Amount B6 (mg) | 1.7 | 0.85 | 0.6375 |
| Amount B12 (mg) | 0.02 | 0.01 | 0.0075 |

TABLE 13

| 15% ALA/NaCl/Vit B Tablet Formulation 70814 | |
|---|---|
| Desired Ingredient List | % Ingredient |
| Neusilin | 2.000 |
| ALA | 15.300 |
| Sodium Chloride | 4.262 |
| NutraTab | 4.145 |
| Calcium Carbonate | 4.138 |
| Kollidan VA-64 Binder | 3.00 |
| Stearic Acid | 1.002 |
| GRS LubriTab (BF) | 5.000 |
| Mg Stearate | 0.500 |
| EmCo Soy | 0.500 |
| Dextrose A | 8.800 |
| Reb A | 0.250 |
| B1 (Thiamine HCL) | 0.075 |
| B6 (Pyridoxine HCL) | 0.085 |
| B12 (Cyanocobalamin - 1% Titration) | 0.100 |
| Flavor | 13.233 |
| DiPac Sugar | 37.60976897 |

CONCLUSION

Compared to the hard candy lozenge version, the compressed tablet form of ALA delivery for orally dissolving administration (which may include sublingual, lingual and/or buccal) may support a higher concentration of ALA without undue ALA burn to the oral tissues (or upper G.I. tract), particularly when paired with NaCl or other BR Salts.

The invention claimed is:

1. An orally dissolvable tablet comprising (a) alpha-lipoic acid in a weight concentration of 12%-45% and (b) a physiologically acceptable salt wherein the weight concentration ratio of the salt to the alpha-lipoic acid in the tablet is in the range between 5% and 200%, wherein the tablet is non-chewable and adapted to be maintained in a recipient's mouth until fully dissolved within 10 minutes following administration.

2. The orally dissolvable tablet of claim 1, wherein the salt is an inorganic salt.

3. The orally dissolvable tablet of claim 2, wherein the salt comprises a sodium cation.

4. The orally dissolvable tablet of claim 3, wherein the salt is sodium chloride.

5. The orally dissolvable tablet of claim 4, wherein the tablet further comprises (1) one or more sugars, (2) one or more sugar substitutes, or (3) a combination of any thereof selected from dextrose, fructose, maltose, isomalt, a directly compressible co-crystallized mixture of about 3% maltodextrin and about 97% sucrose, wherein the one or more sugars, one or more sugar substitutes, or combination of any thereof makes up between about 31% and about 59% of the tablet.

6. An orally administered and orally dissolving formulation comprising alpha-lipoic acid and a salt comprising a cation and an anion, wherein the formulation is non-chewable and is adapted to be maintained in a recipient's mouth until fully dissolved within 10 minutes following administration.

7. The orally administered and orally dissolving formulation of claim 6, wherein (1) the formulation is in the form of a compressed tablet, (2) the alpha-lipoic acid is non-polymerized, (3) the weight concentration of the alpha-lipoic acid in the formulation is in the range between 12% to 45%, and (4) the salt-to-alpha-lipoic acid weight concentration ratio is in the range between 5% to 200%.

8. The orally dissolvable tablet of claim 1, wherein the weight concentration ratio of the salt to the alpha-lipoic acid in the tablet is in the range between 20% and 200%.

9. The orally dissolvable tablet of claim 5, wherein the one or more sugars, one or more sugar substitutes, or combination of any thereof comprises a directly compressible co-crystallized mixture of about 3% maltodextrin and about 97% sucrose.

10. The orally administered and orally dissolving formulation of claim 7, wherein the weight concentration ratio of the salt to the alpha-lipoic acid in the tablet is in the range between 20% and 200%.

11. The orally administered and orally dissolving formulation of claim 7, wherein the weight concentration ratio of the salt to the alpha-lipoic acid in the tablet is in the range between 5% and 100%.

12. The orally administered and orally dissolving formulation of claim 6, wherein the salt is an inorganic salt.

13. The orally administered and orally dissolving formulation of claim 6, wherein the formulation further comprises (1) one or more sugars, (2) one or more sugar substitutes, or (3) a combination of any thereof selected from sucrose, dextrose, fructose, maltose, isomalt, a directly compressible co-crystallized mixture of about 3% maltodextrin and about 97% sucrose, or a combination of any thereof, and whereby the one or more sugars, one or more sugar substitutes, or combination of any thereof reduces the burning associated with the alpha-lipoic acid, increases the bioavailability of the alpha-lipoic acid, or both.

14. An orally administered and orally dissolving formulation comprising alpha-lipoic acid and a salt comprising a cation and an anion, wherein the formulation is non-chewable and is adapted to be dissolved within 10 minutes following administration when maintained in a recipient's mouth.

15. The orally administered and orally dissolving formulation of claim 14, wherein the salt is an inorganic salt.

16. The orally administered and orally dissolving formulation of claim 15, wherein the inorganic salt is sodium chloride.

17. The orally administered and orally dissolving formulation of claim 14, wherein the formulation further comprises (1) one or more sugars, (2) one or more sugar substitutes, or (3) a combination of any thereof selected from sucrose, dextrose, maltose, isomalt, a directly compressible co-crystallized mixture of about 3% maltodextrin and about 97% sucrose, or a combination of any thereof wherein the one or more sugars, one or more sugar substitutes, or combination of any thereof is present in an amount of between about 31% and about 59%.

18. The orally administered and orally dissolving formulation of claim 17, wherein the one or more sugars, one or more sugar substitutes, or combination of any thereof comprises a directly compressible co-crystallized mixture of about 3% maltodextrin and about 97% sucrose.

19. The orally dissolvable tablet of claim 1, wherein the tablet further comprises sodium bicarbonate.

20. The orally dissolvable tablet of claim 1, wherein the tablet is adapted to be maintained in a recipient's mouth until fully dissolved within 3.5 minutes following administration.

21. The orally administered and orally dissolving formulation of claim 6, wherein the formulation further comprises sodium bicarbonate.

22. The orally administered and orally dissolving formulation of claim 6, wherein the formulation is adapted to be maintained in a recipient's mouth until fully dissolved within 3.5 minutes following administration.

23. The orally administered and orally dissolving formulation of claim 14, wherein the formulation further comprises sodium bicarbonate.

24. The orally administered and orally dissolving formulation of claim 14, wherein the formulation is adapted to be maintained in a recipient's mouth until fully dissolved within 3.5 minutes following administration.

25. The orally dissolvable tablet of claim 1, wherein the alpha lipoic acid and the physiologically acceptable salt are distributed in a homogeneous matrix formulation.

* * * * *